United States Patent
Song et al.

(10) Patent No.: US 9,547,377 B2
(45) Date of Patent: Jan. 17, 2017

(54) TRACKBALL MODULE, ULTRASONIC IMAGE PROCESSING APPARATUS USING TRACKBALL MODULE AND METHOD OF CONTROLLING ULTRASONIC IMAGE PROCESSING APPARATUS USING TRACKBALL MODULE

(71) Applicant: SAMSUNG MEDISON CO., LTD., Gangwon-do (KR)

(72) Inventors: Jung Sik Song, Seoul (KR); Soon Deok Kim, Uijeongbu-si (KR); Sung Hyeok Won, Seongnam-si (KR); Gil-ju Jin, Seoul (KR)

(73) Assignee: SAMSUNG MEDISON CO., LTD., Gangwon-Do (KR)

( * ) Notice: Subject to any disclaimer, the term of this patent is extended or adjusted under 35 U.S.C. 154(b) by 448 days.

(21) Appl. No.: 14/084,220

(22) Filed: Nov. 19, 2013

(65) Prior Publication Data
US 2014/0140175 A1 May 22, 2014

(30) Foreign Application Priority Data
Nov. 19, 2012 (KR) .................. 10-2012-0130805

(51) Int. Cl.
*G06F 3/03* (2006.01)
*A61B 8/00* (2006.01)
(Continued)

(52) U.S. Cl.
CPC ............. *G06F 3/0312* (2013.01); *A61B 8/467* (2013.01); *G01S 15/89* (2013.01);
(Continued)

(58) Field of Classification Search
CPC .............................. G06F 3/0312; G06F 3/033
(Continued)

(56) References Cited

U.S. PATENT DOCUMENTS 6,992,653 B2    1/2006    Wang et al.
2005/0248535 A1*  11/2005  Sawyer .................. G06F 3/0312
                                                        345/167
(Continued)

FOREIGN PATENT DOCUMENTS

JP    2010-259678 A    11/2010
JP    2011-141834 A    7/2011
(Continued)

OTHER PUBLICATIONS

Extended European Search Report issued in European Patent Application No. EP 13192843.4 dated Feb. 26, 2014.

*Primary Examiner* — Karabi Guharay
(74) *Attorney, Agent, or Firm* — McDermott Will & Emery LLP

(57) ABSTRACT

An ultrasonic image processing apparatus includes a trackball module configured to receive a control command from a user, and a controller configured to generate a control command for the trackball module and transfers the generated control signal to the trackball module. The trackball module includes a trackball configured to receive a control command from a user, and a lighting device. The lighting device includes a light source, an optical passage bent at least once to provide an optical path through which light emitted from the light source passes while being reflected at least once, and a light exit opening defined at one end of the optical passage from which light passing through the optical passage is emitted to an outside of the lighting device. The light exit opening is defined around the trackball.

9 Claims, 11 Drawing Sheets

(51) Int. Cl.
*G06F 3/0354* (2013.01)
*G01S 15/89* (2006.01)
*A61B 8/08* (2006.01)

(52) U.S. Cl.
CPC .......... *G06F 3/03549* (2013.01); *A61B 8/488* (2013.01); *H01H 2219/0622* (2013.01)

(58) Field of Classification Search
USPC .................................................. 345/167, 170
See application file for complete search history.

(56) References Cited

U.S. PATENT DOCUMENTS

| | | |
|---|---|---|
| 2006/0203485 A1 | 9/2006 | Fu et al. |
| 2007/0083115 A1 | 4/2007 | Lee et al. |
| 2008/0242983 A1 | 10/2008 | Hibi |

FOREIGN PATENT DOCUMENTS

| | | |
|---|---|---|
| KR | 10-2011-0101021 A | 9/2011 |
| KR | 10-2012-0079024 A | 7/2012 |

\* cited by examiner

TRACKBALL MODULE, ULTRASONIC IMAGE PROCESSING APPARATUS USING TRACKBALL MODULE AND METHOD OF CONTROLLING ULTRASONIC IMAGE PROCESSING APPARATUS USING TRACKBALL MODULE

CROSS-REFERENCE TO RELATED APPLICATION

This application claims benefit of priority to Korean Patent Application No. 2012-0130805, filed on Nov. 19, 2012 in the Korean Intellectual Property Office, the entire contents of which are hereby incorporated by reference.

TECHNICAL FIELD

The present inventive concept relates to a trackball module, an ultrasonic image processing apparatus using the trackball module, and a method of controlling an external device or an ultrasonic imaging device connected to the trackball module using the trackball module.

BACKGROUND

An ultrasonic image processing apparatus irradiates ultrasonic waves from the surface of an object, for example, the human body, toward a target region within the body, receives reflected ultrasonic waves reflected by the target region, and obtains tomograms of various tissues and structures, for example, ultrasonic images of soft tissues or blood stream, using the received ultrasonic information.

The ultrasonic image processing apparatus is small in size and low in cost, displays an image in real time and provides high safety owing to no X-ray exposure, or the like, as compared with other imaging devices, such as a digital radiography (DR) system or a computed tomography (CT) scanner. Therefore, the ultrasonic image processing apparatus is widely used for heart diagnosis, abdominal diagnosis, urological diagnosis and obstetric and gynecological diagnosis.

Particularly, when ultrasonic waves generated in transducers disposed at one end of an ultrasonic probe of an ultrasonic image processing apparatus are reflected by a specific interior material of an object, the ultrasonic image processing apparatus performs beam forming by receiving the reflected ultrasonic waves, converting the received ultrasonic waves into electrical signals, and compensating for a time difference between the electrical signals, and then produces an ultrasonic image through predetermined image processing.

SUMMARY

Therefore, an aspect of the present inventive concept relates to a trackball module including a lighting device to reduce eye fatigue, an ultrasonic image processing apparatus including the trackball module, and a method of controlling the trackball module and the ultrasonic image processing apparatus.

Another aspect of the present inventive concept relates to reducing of eye fatigue caused by direct lighting of a user control panel of an ultrasonic image processing apparatus conventionally used in a dark room.

A further aspect of the present inventive concept relates to reducing of glare of a lighting device around a trackball of an ultrasonic image processing apparatus.

A further aspect of the present inventive concept relates to lighting of a lighting device in various colors and patterns to allow a user to intuitively recognize a current status of an ultrasonic image processing apparatus.

A further aspect of the present inventive concept relates to providing of emotional security to a long term user of an ultrasonic image processing apparatus such as a sonographer since a lighting device emits dim light.

Additional aspects of the inventive concept will be set forth in part in the description which follows and, in part, will be obvious from the description, or may be learned by practice of the inventive concept.

Aspects of the present inventive concept relate to a trackball module, an ultrasonic image processing apparatus connected to the trackball module or including the trackball module, and a method of controlling the ultrasonic image processing apparatus using the trackball module are provided.

One aspect of the present inventive concept encompasses a trackball module including a trackball configured to receive a control command from a user and a lighting device configured to emit light. The lighting device includes a light source, an optical passage bent at least once to provide an optical path through which light emitted from the light source passes while being reflected at least once, and a light exit opening defined at one end of the optical passage from which light passing through the optical passage is emitted to an outside of the lighting device. The light exit opening is defined around the trackball.

The light source may be mounted at a portion of the optical passage. The light source may be disposed at the other end of the optical passage opposite to the light exit opening.

The light source may maintain output of light, blink, or cease output of light according to a setting mode. The light source may emit with different colors according the setting mode or user manipulation of the trackball.

The light source may emit light while an external device connected thereto operates, emit light as a pulse while waiting for a subsequent operation after completion of a previous operation, and stop emitting of light while all operations are stopped, according to a setting mode.

The optical passage may be bent toward the trackball or in a direction opposite to the trackball. A reflective element reflecting light emitted from the light source may be disposed in the optical passage.

The light exit opening may be sealed by a cover that transmits light.

Another aspect of the present inventive concept relates to an ultrasonic image processing apparatus including an ultrasonic probe configured to irradiate ultrasonic waves to an object, receive ultrasonic waves reflected by the object, convert the received ultrasonic waves, and output a plurality of ultrasonic signals, an image processor configured to perform beam forming of the plurality of ultrasonic signals and generate ultrasonic image data based on results of the beam forming, a trackball module configured to receive a control command from a user, and a controller configured to generate a control command for the trackball module and transfer the generated control command to the trackball module.

The trackball module includes a trackball configured to receive a control command from a user and a lighting device. The lighting device includes a light source, an optical passage bent at least once to provide an optical path through which light emitted from the light source passes while being reflected at least once, and a light exit opening defined at one end of the optical passage from which light passing through the optical passage is emitted to an outside of the lighting device.

The light exit opening is defined around the trackball.

The light source of the ultrasonic image processing apparatus may be disposed at a portion of the optical passage. The light source may be disposed at the other end of the optical passage opposite to the light exit opening.

The light source may be controlled to continuously emit light, blink, or cease output of light according to a setting mode of the ultrasonic image processing apparatus.

The light source may emit light with different colors in accordance with a setting mode of the ultrasonic image processing apparatus or user manipulation of the trackball.

The light source may emit light while the ultrasonic image processing apparatus operates according to at least one setting mode selected from a plurality of setting modes of the ultrasonic image processing apparatus, the light source may emit light as a pulse while the ultrasonic image processing apparatus completes an operation according to the selected setting mode and waits for a subsequent operation, and the light source may not emit light while the ultrasonic image processing apparatus does not operate. The at least one setting mode may be selected by a user.

When Doppler ultrasound using Doppler effects is used in the ultrasonic image processing apparatus, the light source is configured to control output of light in accordance with existence of sound of the Doppler ultrasound or volume of the sound.

The optical passage may be bent toward the trackball or in a direction opposite to the trackball. A reflective element reflecting light emitted from the light source may be disposed in the optical passage.

The light exit opening may be sealed by a cover that transmits light.

Another aspect of the present inventive concept encompasses a method of controlling an ultrasonic image processing apparatus including a trackball module or connected to the trackball by use of the trackball module. According to the method, at least one setting mode from a plurality of setting modes is selected. A light source is controlled to emit light by supplying power to the light source while the ultrasonic image processing apparatus operates in accordance with the selected at least one setting mode. The light source is controlled to blink by supplying power to the light source as a pulse while the ultrasonic image processing apparatus completes an operation according to the selected at least one setting mode and waits for a subsequent operation.

The ultrasonic image processing apparatus includes a trackball configured to receive a control command from a user and a lighting device, wherein the lighting device includes a light source, an optical passage bent at least once to provide an optical path through which light emitted from the light source passes while being reflected at least once, and a light exit opening defined at one end of the optical passage from which light passing through the optical passage is emitted to an outside of the lighting device. The light exit opening is defined around the trackball.

The method may further include turning off the light source by blocking power to the light source while the at least one setting mode is not selected from the plurality of setting modes.

BRIEF DESCRIPTION OF THE DRAWINGS

The foregoing and other features of the inventive concept will be apparent from more particular description of embodiments of the inventive concept, as illustrated in the accompanying drawings in which like reference characters may refer to the same or similar parts throughout the different views. The drawings are not necessarily to scale, emphasis instead being placed upon illustrating the principles of the embodiments of the inventive concept. In the drawings, the thickness of layers and regions may be exaggerated for clarity.

DETAILED DESCRIPTION

Figure 1:
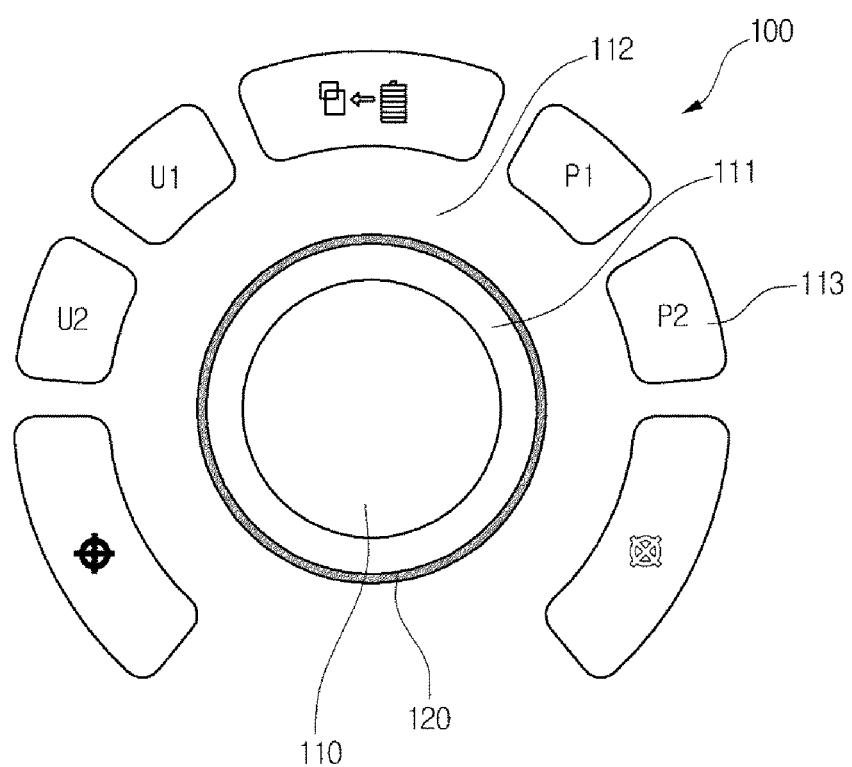
FIG. 1 is a front view illustrating a trackball module according to an embodiment of the present inventive concept.

Examples of the present inventive concept will be described below in more detail with reference to the accompanying drawings. The examples of the present inventive concept may, however, be embodied in different forms and should not be construed as limited to the examples set forth herein. Like reference numerals may refer to like elements throughout the specification.

FIG. 1 is a front view illustrating a trackball module 100 according to an embodiment of the present inventive concept.

As illustrated in FIG. 1, the trackball module 100 according to an embodiment of the present inventive concept may include a trackball 110 and a lighting device 120.

The trackball 110 may generate a specific electrical signal according to user manipulation by use of a fingertip or a palm and transmit the electrical signal to a controller, or the like, to control various devices such as computers or ultrasonic image processing apparatuses. The trackball 110 may have a circular shape, a quadrangular shape, or a quadrangular shape with rounded corners from a top view and may have a semicircular shape, a trapezoidal shape, or a rectangular shape from a side view. When a user touches the trackball 110 with a fingertip or a palm and rotates the trackball 100 in a predetermined direction, or when the user performs an operation similar to rotating the trackball 110 with the fingertip or the palm in a state of being touched, the trackball 110 may generate an electrical signal in response to user manipulation, for example, an electrical signal regarding movement of a pointer displayed on a display screen. A processor connected to the trackball 110 may generate a command for a device connected to the trackball module 100 according to the generated electrical signal to operate the device connected to the trackball module 100.

The lighting device 120 may guide the user to a location of the trackball 110 by emitting light around the trackball 110 or may indicate a current status of an external device controlled by the trackball module 100, for example, a computer or an ultrasonic image processing apparatus.

The lighting device 120 may include a light source, an optical passage, and a light exit opening. In this regard, the optical passage may be bent at least once and provide an optical path through which light emitted from the light source passes while being reflected at least once. The light exit opening may be disposed at one end of the optical passage from which light that has passed through the optical passage is emitted to the outside. Here, the light exit opening may be formed around the trackball 110. These will be described later.

The trackball module 100 may further include a support 111 on which the trackball 110 is mounted and a side portion 112 at which a separate control button 113 is mounted. In this regard, the lighting device 120 may be disposed between the support 111 and the side portion 112.

The trackball module 100 may further include an input device 113 to control an external device such as a computer or an ultrasonic image processing apparatus, for example, a button-like input device 113 as illustrated in FIG. 1. Via the input device 113, the user may select at least one setting mode among a plurality of setting modes to control an external device such as a computer or an ultrasonic image processing apparatus, as occasion demands.

The input device 113 may indicate, for example, by carving and printing thereon, symbols and characters that distinguish one input device 113, e.g., one button, from another input device 113, e.g., another button, or display a status of an operation performed by the external device in response to clinking or touch of a button.

According to an embodiment of the present inventive concept, the input device 113 may be provided with a light emitting device, for example, a light emitting diode (LED) at a rear end thereof to improve readability of characters and symbols displayed on the input device 113. Alternatively, the symbols or characters may be printed on the input device 113 using a fluorescent material to further improve readability.

Figure 2:
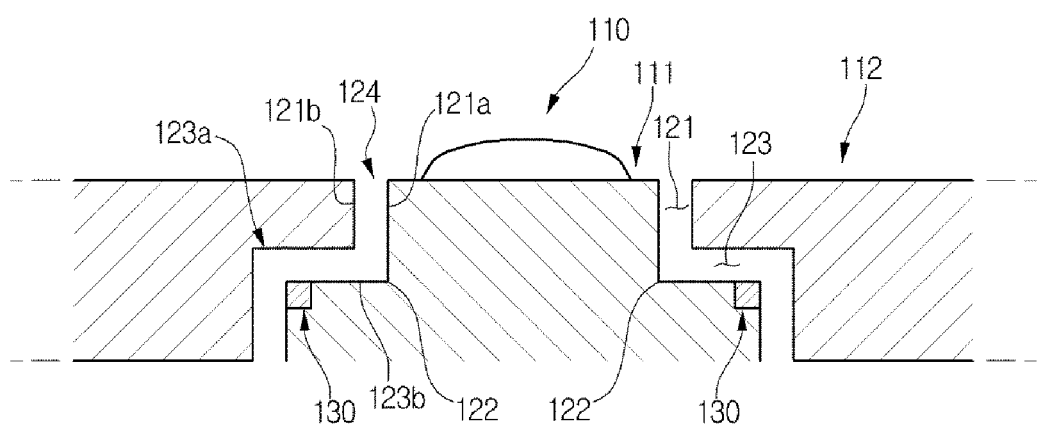
FIG. 2 is a cross-sectional view illustrating a trackball module according to an embodiment of the present inventive concept.

FIG. 2 is a cross-sectional view illustrating a trackball module 100 according to an embodiment of the present inventive concept.

As illustrated in FIG. 2, the trackball module 100 may include a lighting device 120. The lighting device 120 may include a light source 130, an optical passage 121 to 123 through which light emitted from the light source 130 passes, and a light exit opening 124 disposed at one end of the optical passage 121 to 123.

The light source 130 may generate light according to a voltage applied thereto. The light source 130 may be any light emitting device that generates light and emits the light. For example, the light source 130 may be selected from an incandescent electric lamp using a filament formed of tungsten, a fluorescent lamp using a fluorescent material, and an LED lamp using a semiconductor device that emits light according to a voltage applied thereto. In addition, the light source 130 may be a combination of at least two thereof.

According to an embodiment of the present inventive concept, when the lighting device 120 includes a plurality of light sources 130, the same light source, e.g., an LED, or different light sources may be used as the light source 130.

In addition, the light source 130 may generate light with a predetermined color, such as light bulb color, warm white, white, bright white, red, or blue. The light source 130 may also generate light with various colors. Particularly, color of light emitted from the light source 130 may vary according to an external control command.

Light emitted from the light source 130 may pass through the optical passage 121 to 123 to be emitted outward via the light exit opening 124.

The optical passage 121 to 123 that is a path through which light emitted from the light source 130 passes may be bent at least once as shown in FIG. 2 to prevent the light generated in the light source 130 from being directly emitted to the outside. For example, the optical passage 121 to 123 may be bent in a direction opposite to the trackball 110 as illustrated in FIG. 2.

According to an embodiment of the present inventive concept, the optical passage 121 to 123 may be bent once at a bent portion 122 as illustrated in FIG. 2.

In this regard, the optical passage 121 to 123 may be divided into a first passage 121 and a second passage 123 by the bent portion 122. The light exit opening 124 may be formed at one end of the first passage 121, and the other end of the first passage 121 may be connected to the second passage 123 via the bent portion 122. Here, one end of the second passage 123 may be connected to the other end of the first passage 121 via the bent portion 122, and the light source 130 may be formed at a predetermined portion of the second passage 123, for example, the other end of the second passage 123. According to an embodiment of the present inventive concept, the light source 130 may be disposed not only at the end of the second passage 123 but also within the second passage 123. In addition, the light source 130 may be installed at an inner wall, particularly, at an upper inner wall 123*a* of the second passage 123 or at a lower inner wall 123*b* as illustrated in FIG. 2. Although not shown in the drawings, when the optical passage 121 to 123 has a tunnel shape, the light source 130 may also be installed at a side surface of the second passage 123.

When the light source 130 disposed at a predetermined position of the optical passage 121 to 123, for example, at the other end of the second passage 123, irradiates light, the light may arrive at the light exit opening 124 via the optical passage 121 to 123, for example, the second passage 123, the bent portion 122, and the first passage 121.

In this regard, light irradiated from the light source 130 into the optical passage 121 to 123, particularly, into the second passage 123, may be reflected at least once by the second passage 123 or the first passage 121 and emitted via the light exit opening 124 since the optical passage 121 to 123 is bent at least once. For example, light emitted from the light source 130 may arrive at the light exit opening 124 disposed at the end of the first passage 121 after being reflected at least once by the inner walls 123*a* and 123*b* of the second passage 123. Alternatively, the light may arrive at inner walls 121*a* and 121*b* of the first passage 121 and then reflected by the inner walls 121*a* and 121*b* of the first passage 121 at least once to arrive at the light exit opening 124.

In other words, light emitted from the light source 130 may not be directly emitted to the outside via the light exit opening 124 but emitted outward after being reflected at least once. Thus, light emitted to the outside may have a relatively lower intensity than light directly emitted from the light source 130. Thus, light emitted from the light exit opening 124 may also have low glare, thereby reducing eye fatigue.

The optical passage 121 to 123 may have a circular tunnel shape or a step-like shape formed between two plates, for example, between the support 111 and the side portion 112.

In this regard, the support 111 may have a step-like shape by disposing a circular plate with a smaller diameter on a circular plate with a larger diameter. The side portion 112 may have a shape corresponding to the step-like shape of the support 111, thereby forming the optical passage 121 to 123 between the support 111 and the side portion 112.

The light exit opening 124 may be formed at one end of the optical passage 121 to 123, for example, one end of the first passage 121, to emit light reflected in the optical passage 121 to 123 outward. The light exit opening 124 may be formed around the trackball 110.

Figure 3A:
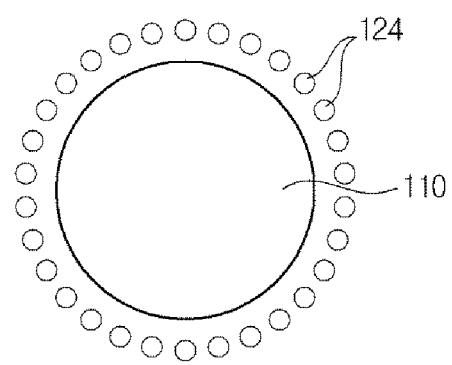
FIGS. 3A and 3B are diagrams illustrating examples of a light exit opening of a trackball module.
Figure 3B:
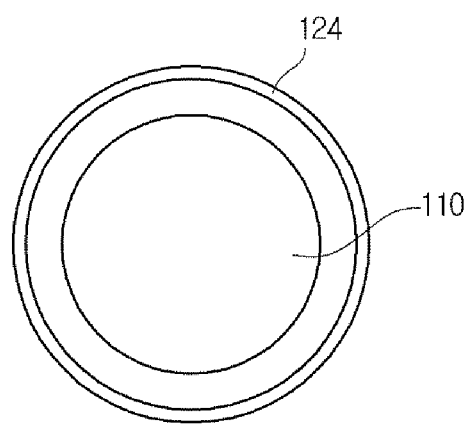

FIGS. 3A and 3B are diagrams illustrating examples of a light exit opening 124 of a trackball module.

As illustrated in FIG. 3A, according to an embodiment of the present inventive concept, the light exit openings 124 may be formed as circular holes aligned along a circle surrounding the trackball 110. In this case, the optical passage 121 to 123 may have a tunnel shape with a circular cross-section in accordance with the shape of the light exit openings 124. Alternatively, the optical passage 121 to 123 may have a step-like shape as described above.

In addition, according to an embodiment of the present inventive concept, the light exit opening 124 may be formed in a circular track surrounding the trackball 110 as illustrated in FIG. 3B. When the trackball 110 has a circular shape from a top view as illustrated in FIG. 3B, the light exit opening 124 may be aligned in a circular track form that is a concentric circle to the trackball 110. In this case, the optical passage 121 to 123 may have a step-like shape as described above.

Figure 4A:
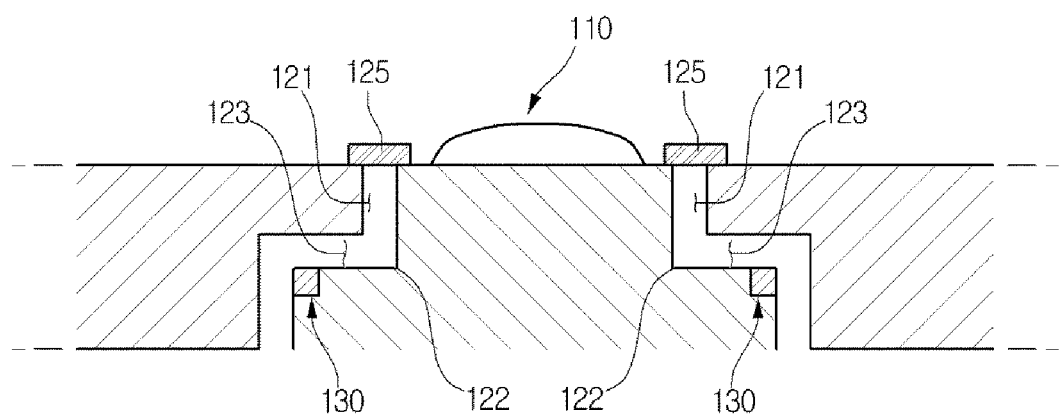
FIGS. 4A to 4C are cross-sectional views illustrating trackball modules according to embodiments of the present inventive concept.
Figure 4B:
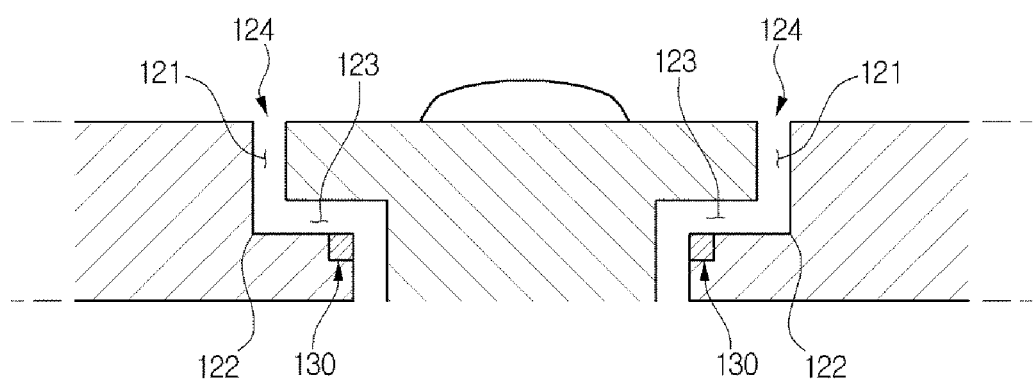
Figure 4C:
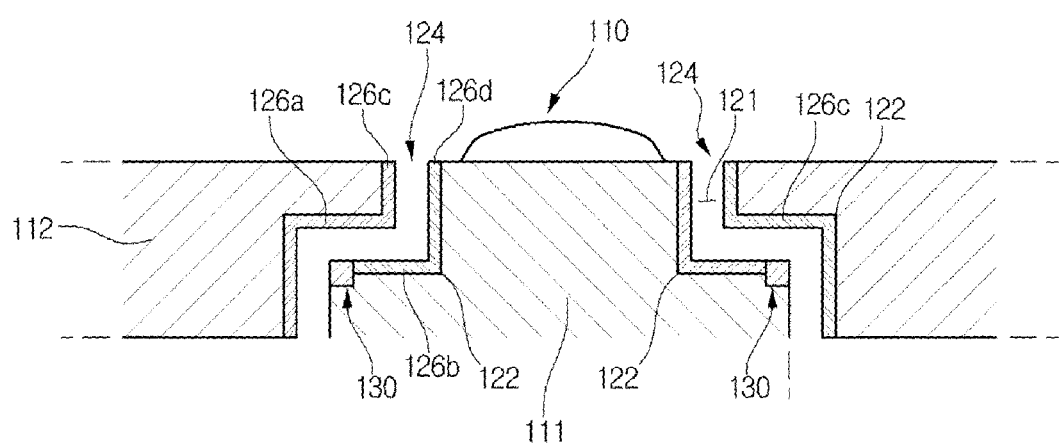

FIGS. 4A to 4C are cross-sectional views illustrating trackball modules according to embodiments of the present inventive concept.

According to an embodiment of the present inventive concept, in the trackball module 100 as illustrated in FIG. 4A, the upper end of the light exit opening 124 of the trackball module 100 may be sealed by a cover 125. The cover 125 may seal the light exit opening 124 and transmit light that has passed through the optical passage 121 to 123. Accordingly, the cover 125 may be formed of various materials uniformly transmitting light, for example, glass or a transparent synthetic resin.

As occasion demands, the cover 125 may have a predetermined color, such as red, green, blue, and white. In this regard, the color of light visible to a user through the lighting device 120 may be determined by color of light emitted from the light source 130 and color of the cover 125.

According to another embodiment of the present inventive concept, in the trackball module 100, the bent portion 122 of the optical passage 121 to 123 may be in a state of being bent toward the trackball 110 as illustrated in FIG. 4B in a different manner from that of FIG. 2.

According to another embodiment of the present inventive concept, in the trackball module 100, an inner wall of the optical passage 121 to 123 may be coated with a material capable of reflecting predetermined light or provided with a reflective element 126a to 126d, e.g., a reflective mirror, capable of reflecting predetermined light. Reflectivity of light may be very low according to a material used to form the support 111 and the side portion 112 as illustrated in FIG. 4C. In this case, energy of light generated in the light source 130 may be reduced after being emitted via the light exit opening 124 so as to be insufficient to allow a user to see. In addition, in order to emit light having energy sufficient to allow a user to see through the light exit opening 124, power supplied to the light source 130 may be increased. Accordingly, light having sufficient energy may be emitted via the light exit opening 124 by coating a highly reflective material on the inner wall of the optical passage 121 to 123 or installing the reflective element 126a to 126d, or the like thereto.

According to an embodiment of the present inventive concept, the optical passage 121 to 123 may have the same width as the light exit opening 124. According to another embodiment of the present inventive concept, the light exit opening 124 may have a smaller width than that of the optical passage 121 to 123, or vice versa.

Meanwhile, according to an embodiment of the present inventive concept, the optical passage 121 to 123 or the light exit opening 124 may have a width of 1.0 mm or less. As the optical passage 121 to 123 or the light exit opening 124 has a smaller width, glare of the emitted light may be reduced.

Figure 5:
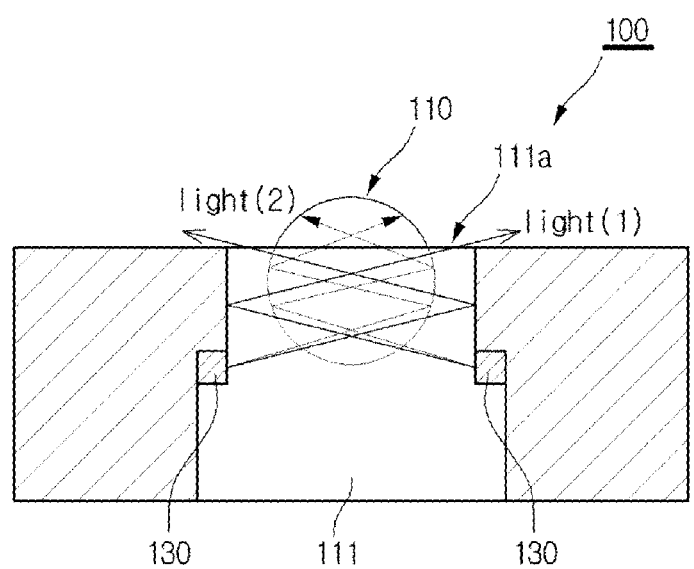
FIG. 5 is a cross-sectional view illustrating a trackball module according to another embodiment of the present inventive concept.

FIG. 5 is a cross-sectional view illustrating a trackball module according to another embodiment of the present inventive concept.

A trackball module according to an embodiment of the present inventive concept, as illustrated in FIG. 5, may include a light source 130 emitting light, a support 111 at which the trackball 110 is mounted, and a trackball 110 receiving a control command from a user.

The light source 130 may be mounted at a predetermined position in the trackball module 100. According to an embodiment of the present inventive concept, the light source 130 may be mounted at the support 111 or at a bent portion of the support 111 as illustrated in FIG. 5.

The support 111 may support the light source 130 and/or the trackball 110. According to an embodiment of the present inventive concept, both the light source 130 and the trackball 110 may be mounted at the support 111. Alternatively, only the trackball 110 may be mounted at the support 111.

Light emitted from the light source 130 may pass through the support 111 to be emitted to the outside from a light exit surface 111a formed at one end of the support 111 as illustrated in FIG. 5. In this case, light emitted from the light source 130 may arrive at the light exit surface 111a after being reflected at least once within the support 111 and may be emitted to the outside. Thus, the support 111 may function as the optical passage 121 to 123 described above, and the light exit surface 111a may function as the light exit opening 124 described above.

The support 111 may be formed of a transparent material with a predetermined transmittance to allow light transmission, for example, a transparent synthetic region or glass. Alternatively, the support 111 may be formed of a semi-transparent material.

The trackball 110 may receive a predetermined control command from a user as described above.

The trackball 110 may be mounted at a predetermined position of the light exit surface 111a of the support 111, for example, at the center of the light exit surface 111a, and supported by the support 111. The side of the trackball 110 may be configured such that light emitted from the light source 130 may be emitted to the outside from the side of the trackball 110 since a portion of the support 111, i.e., a portion of the light exit surface 111a is exposed to the outside as illustrated in FIG. 5 (light 1).

According to an embodiment of the present inventive concept, the trackball 110 may be formed of an opaque material to block transmission of light, which is emitted from the light source 130, through the trackball 110. In this case, light emitted from the light source 130 may be emitted to the outside via only the light exit surface 111a exposed at a side of the trackball 110.

According to another embodiment of the present inventive concept, the trackball 110 may be formed of a semi-transparent material to allow light emitted from the light source 130 to partially pass through the trackball 110. That is, light emitted from the light source 130 cannot completely pass through the trackball 110 but may be emitted through the trackball 110. In this case, in addition to light emitted via the light exit surface 111a at the side of the trackball 110, light may be partially emitted through the trackball 110 as illustrated in FIG. 5 (light 2). When the trackball 110 is semi-transparent, intensity of light emitted through the trackball 110 may be adjusted to be less than that of light emitted through the light exit surface 111a, while various circuits aligned at the rear side of the trackball 110 are not visible.

Figure 6:
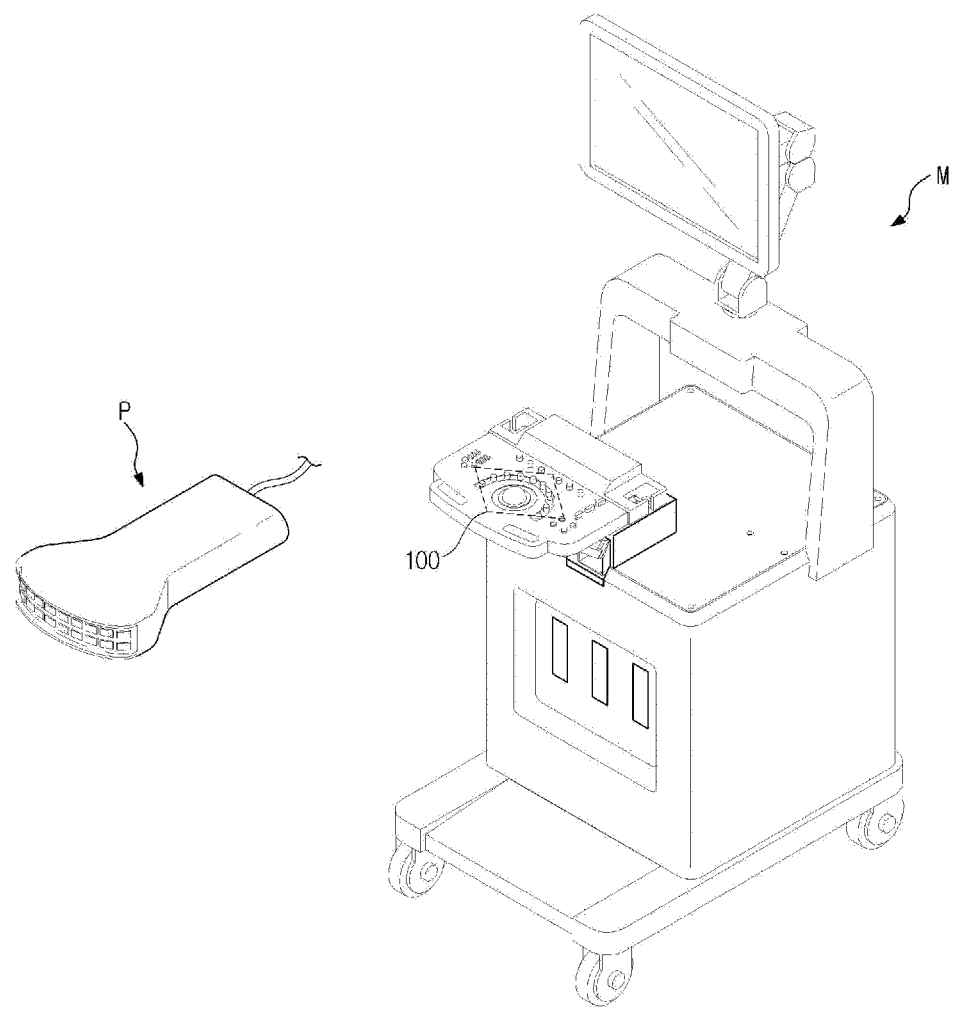
FIG. 6 is a perspective view illustrating an ultrasonic image processing apparatus according to an embodiment of the present inventive concept.

FIG. 6 is a perspective view illustrating an ultrasonic image processing apparatus according to an embodiment of the present inventive concept.

Referring to FIG. 6, an ultrasonic image processing apparatus according to an embodiment of the present inventive concept, may include an ultrasonic probe p and a main body m.

The ultrasonic probe p may generate ultrasonic waves and irradiate the ultrasonic waves to an object, for example, the human body. The ultrasonic waves may be reflected by an internal substance located at various depths, i.e., a target substance. The ultrasonic probe p may receive the reflected ultrasonic waves. An ultrasonic image may be produced based on the received ultrasonic waves.

The ultrasonic probe p may include, at one end thereof, a plurality of ultrasonic transducers that generate ultrasonic waves in accordance with a supply voltage applied thereto, receive ultrasonic waves reflected by the internal substance of the object, and convert the received ultrasonic waves into electrical signals. The ultrasonic transducers may receive AC power from an external power supply device or an internal power storage device, for example, a battery, to generate ultrasonic waves by vibration of piezoelectric vibrators or thin films of the ultrasonic transducers according to the applied AC power. In addition, the ultrasonic transducers may receive the reflected ultrasonic waves. Piezoelectric vibrators or thin films of the ultrasonic transducers may vibrate upon receiving the reflected ultrasonic waves to generate electrical signals.

The ultrasonic transducers of the ultrasonic probe p may be classified into magnetostrictive ultrasonic transducers, piezoelectric ultrasonic transducers, and capacitive micromachined ultrasonic transducers (cMUTs) according to materials used therefor or properties of the materials.

When the ultrasonic probe p receives reflected ultrasonic waves, the ultrasonic probe p or the main body m may perform a predetermined process with respect to the converted electrical signals to produce an ultrasonic image. Accordingly, a user, such as, a doctor or a nurse, may diagnose a patient using an image showing the interior of a patient's body.

Although not shown in the drawings, a trackball module 100 may be provided at the ultrasonic probe p. When the ultrasonic probe p is provided with the trackball module 100, the user may control the ultrasonic image processing apparatus using the trackball module 100 while grabbing the ultrasonic probe p.

According to an embodiment of the present inventive concept, the main body m may produce an ultrasonic image based on ultrasonic waves received by the ultrasonic probe p and display the ultrasonic image to the user via a display device or the like. In addition, the main body m may include a trackball module 100 as an input device capable of receiving a predetermined instruction or command from the user as illustrated in FIG. 6. The main body m may control irradiation of ultrasonic waves by the ultrasonic probe p or acquire an ultrasonic image by changing a setting mode for obtaining an ultrasonic image according to an instruction or command input through a user interface such as the trackball module 100 or another input device, for example, a mouse or a keyboard.

Figure 7:
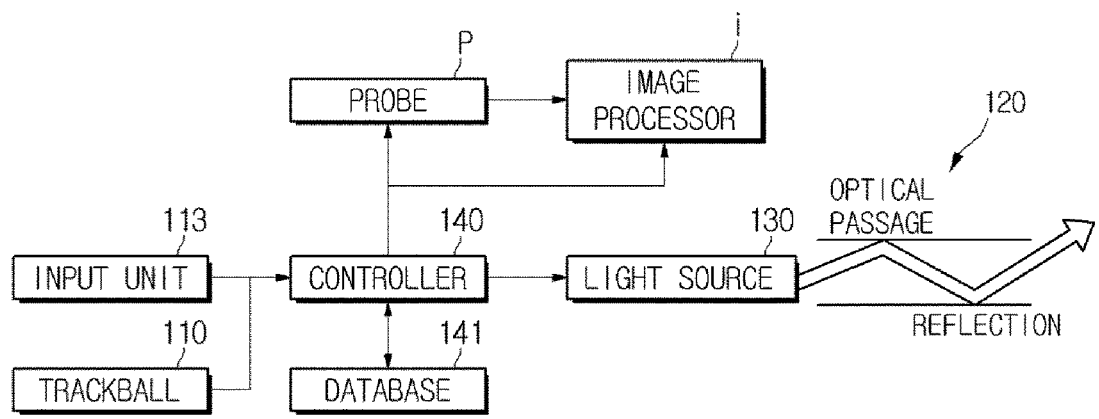
FIG. 7 is a block diagram illustrating an ultrasonic image processing apparatus including a trackball module according to an embodiment of the present inventive concept.

FIG. 7 is a block diagram illustrating an ultrasonic image processing apparatus including a trackball module according to an embodiment of the present inventive concept.

As illustrated in FIG. 7, the ultrasonic image processing apparatus may include an ultrasonic probe p, an image processor i, which performs beam forming of a plurality of ultrasonic signals and generates ultrasonic image data based on the results of the beam forming, a trackball 110 of a trackball module 100 receiving a user's command or an input device 113 mounted in the trackball module 100 or separately disposed therefrom and receiving a user's command, a controller 140 controlling other constituent elements according to an instruction or a command input to the input device 113, and a database 141 connected to the controller 140 and storing information about various setting modes.

The ultrasonic image processing apparatus may include a light source 130 mounted at the trackball module 100 and an optical passage 120 through which light emitted from the light source 130 passes while being reflected. Although not shown in the drawings, the optical passage 120 may be bent at least once as described above.

As illustrated in FIG. 7, the user may input an instruction or command via the input device 113 or the trackball 110 of the trackball module 100. In this regard, the user may select at least one setting mode among a plurality of setting modes to perform operations of the ultrasonic image processing apparatus, for example, control of the imaging process or among a plurality of setting modes to control the lighting device 120 of the trackball module 100. Thus, the user may select a setting mode for the lighting device 120 of the trackball module 100, such that the light source 130 of the trackball module 100 continuously emits light, blinks, or ceases output of light.

As such, the instruction or command inputted by the user via the input device 113 or the trackball 110 of the trackball module 100 may be transferred to the controller 140.

The controller 140 may control operation of the ultrasonic probe p of the ultrasonic image processing apparatus or operation of the image processor i, which generates an ultrasonic image, based on the received ultrasonic waves via the ultrasonic probe p. According to an embodiment of the present inventive concept, the controller 140 may control the lighting device 120 of the trackball module 100, particularly, the light source 130 of the lighting device 120, according to user manipulation or internal settings without being influenced by user manipulation.

According to an embodiment of the present inventive concept, the controller 140 may read the database 141 and select the setting mode for the lighting device 120 of the trackball module 100, for example, the setting mode regarding environments in which the ultrasonic image processing apparatus is used. Then, the controller 140 may generate a control command according to the selected setting mode for the lighting device 120 and transmit the control command to the light source 130. The light source 130 may maintain output of light, blink, or cease output of the light in accordance with the received setting mode for the lighting device 120. Alternatively, the controller 140 may also control the light source 130 to emit light with different colors according to the setting mode for the lighting device 120. For example, when the ultrasonic image processing apparatus is used for obstetric and gynecological diagnosis, the lighting device 120 may emit green light. When the ultrasonic image processing apparatus is used in heart diagnosis, the lighting device 120 may emit red light. When the ultrasonic image processing apparatus is used in radiology, the lighting device 120 may emit blue light.

According to another embodiment of the present inventive concept, the controller 140 may read the database 141 and select the setting mode for an operation of the ultrasonic image processing apparatus, for example, an ultrasonic imaging. The controller 140 may generate a control command in accordance with the selected setting mode for the operation of the ultrasonic image processing apparatus and transmit the control command to the light source 130. The light source 130 may maintain output of light, blink, or cease output of the light in accordance with the received setting mode for the lighting device 120. In the same manner, the controller 140 may also control the light source 130 to emit light with different colors according to the setting mode for the ultrasonic imaging.

According to an embodiment of the present inventive concept as to operation of the lighting device 120 of the trackball module 100 by the controller 140, when the ultrasonic image processing apparatus operates in accordance with a predetermined setting mode, the controller 140 may control to continuously supply power to the light source 130 to allow the light source 130 to continuously emit light. As a result, the lighting device 120 of the trackball module 100 may be continuously lighted.

When the ultrasonic image processing apparatus completes an operation according to the selected setting mode and waits for a subsequent operation, for example, waits for input of a measuring point during real-time ultrasonic scanning, the controller 140 may supply a power to the light source 130 as a pulse with a predetermined frequency such that the light source 130 blinks at a predetermined interval. Accordingly, the lighting device 120 of the trackball module 100 may blink.

In addition, when the ultrasonic image processing apparatus completes or stops all operations, the controller 140 may block power supply to the light source 130 such that the light source 130 does not emit light. As a result, the lighting device 120 of the trackball module 100 may be turned off.

Meanwhile, the ultrasonic image processing apparatus may use Doppler ultrasound based on the Doppler effect. Particularly, when an ultrasonic wave is irradiated to an object moving away from an observer, a reflected ultrasonic wave may have a lower frequency than the irradiated ultrasonic wave. On the other hand, when an ultrasonic wave is irradiated to an object moving toward the observer, the reflected ultrasonic wave may have a higher frequency than the irradiated ultrasonic wave. Doppler ultrasound may be used based on relative difference in frequency between the irradiated ultrasonic wave and the reflected ultrasonic wave when an ultrasonic wave is irradiated to a moving object.

As described above, as Doppler ultrasound using Doppler effects is used, the controller 140 may control light emitted from the light source 130 in accordance with existence of sound of the Doppler ultrasound or volume thereof. For example, light intensity may be increased if there is Doppler ultrasound. In addition, intensity of light emitting from the light source 130 may be controlled in proportion to volume of the sound. Thus, since the lighting device 120 of the trackball 110 visibly expresses according to the existence of Doppler ultrasound or volume of the sound, a user may intuitively recognize movement of an object or velocity of the object via the lighting device 120.

In addition, according to an embodiment of the present inventive concept, the controller 140 may control the light source 130 in accordance with user manipulation of the trackball 110. For example, when the user manipulates the trackball 110, the light source 130 may be controlled to emit light with a predetermined color. When the user does not manipulate the trackball 110, the power to the light source 130 may be off or the light source 130 may be controlled according to the setting mode of the ultrasonic image processing apparatus or operation of the ultrasonic image processing apparatus as described above.

The above description may also be applied to the trackball module 100 installed at the ultrasonic probe p.

Figure 8:
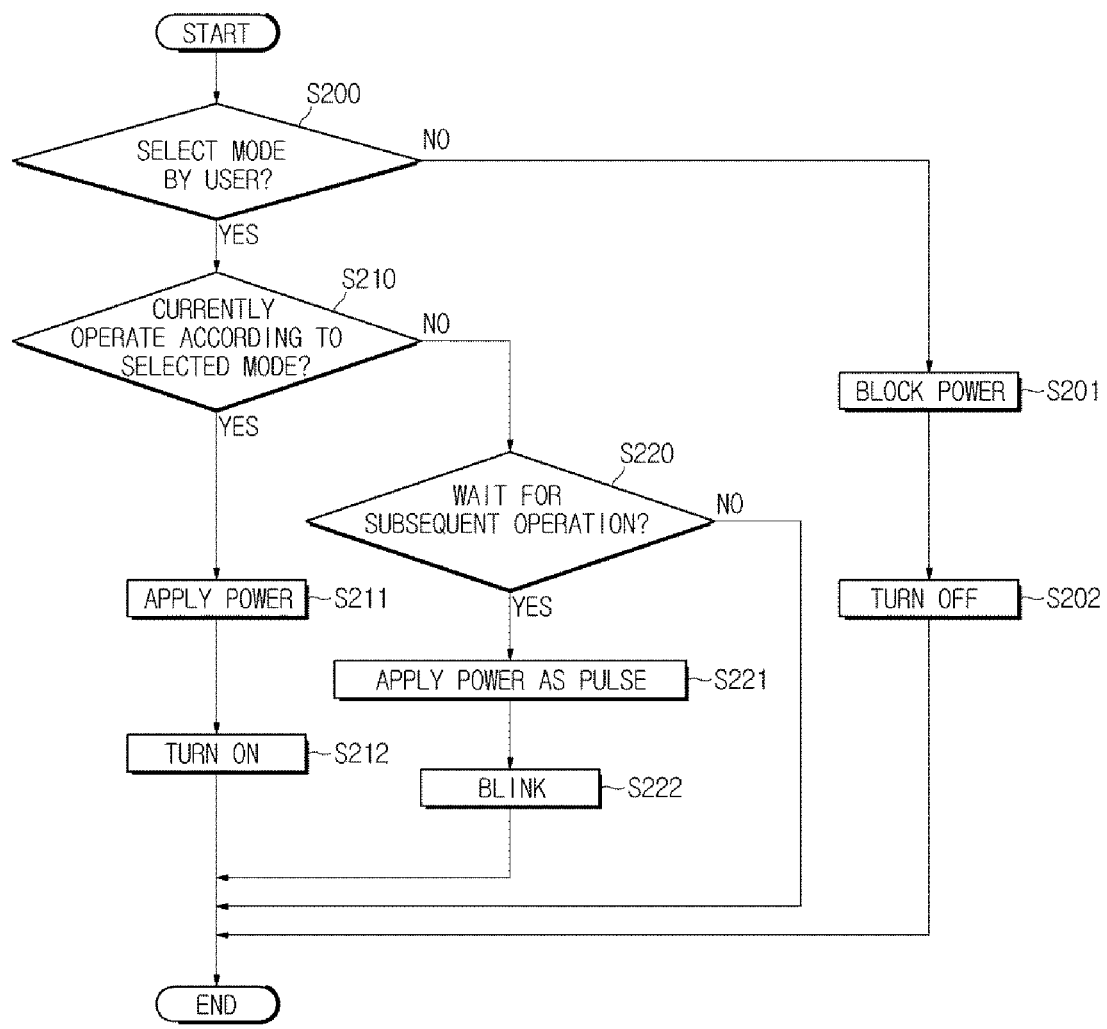
FIG. 8 is a flowchart illustrating a method of controlling a trackball module according to an embodiment of the present inventive concept.

FIG. 8 is a flowchart illustrating a method of controlling a trackball module according to an embodiment of the present inventive concept.

As illustrated in FIG. 8, according to the method of controlling the trackball module, a user may first select at least one setting mode among a plurality of setting modes, for example, a plurality of setting modes for operation of the ultrasonic image processing apparatus (S200).

Then, the ultrasonic image processing apparatus may operate according to the selected setting mode by the user (S210). When the ultrasonic image processing apparatus operates according to the at least one setting mode, power may be supplied to the light source 130 (S211). Then, the light source 130 may emit light to turn on the lighting device 120 (S212). In this regard, light emitted from the light source 130 may pass through the optical passage 121 to 123, which may be bent at least once, to be emitted to the outside via the light exit opening 124 as described above. Thus, eye fatigue of the user viewing the lighting device 120 may be reduced.

The ultrasonic image processing apparatus may complete the operation according to the selected at least one setting mode and wait for a subsequent operation (S220). In this case, power may be supplied to the light source 130 as a pulse (S221). Thus, the light source 130 may blink. As a result, the lighting device 120 may also blink (S222).

When the at least one setting mode is not selected from the plurality of setting modes or the ultrasonic image processing apparatus does not operate (when the determination of S200 is No), a power to the light source 130 may be off (S201). As a result, the light source 130 is turned off, and the lighting device 120 may not emit light (S202).

Thus, the user may easily recognize a current status of operation of the ultrasonic image processing apparatus without glare.

As is apparent from the above description, a trackball module, an ultrasonic image processing apparatus including the trackball module, and a method of controlling the trackball module and the ultrasonic image processing apparatus are provided. When the trackball module and the ultrasonic image processing apparatus using the same are used, eye fatigue caused by direct lighting of a user control panel may be reduced.

Particularly, eye fatigue may be reduced by decreasing glare by the lighting device disposed around the trackball of the ultrasonic image processing apparatus.

Furthermore, the user may recognize a current status of the ultrasonic image processing apparatus by controlling the lighting device of the trackball module to emit various colors.

In addition, since the lighting device emits dim light, a long term user of an ultrasonic image processing apparatus such as a sonographer may have emotional security.

Although a few embodiments of the present inventive concept have been shown and described, it would be appreciated by those skilled in the art that changes may be made in these embodiments without departing from the principles and spirit of the inventive concept, the scope of which is defined in the claims and their equivalents.

What is claimed is:

1. A trackball module, comprising:
 a trackball configured to receive a control command from a user; and
 a lighting device configured to emit light,
 wherein the lighting device comprises:
  a light source;
  an optical passage bent at least once to provide an optical path through which light emitted from the light source passes while being reflected at least once; and
  a light exit opening defined at one end of the optical passage from which light passing through the optical passage is emitted to an outside of the lighting device,
 wherein the light exit opening is defined around the trackball, and
 wherein the optical passage has a step-like shape formed between two plates.

2. The trackball module according to claim 1, wherein the optical passage is bent toward the trackball or in a direction opposite to the trackball.

3. The trackball module according to claim 1, wherein the light source is disposed at the other end of the optical passage opposite to the one end at which the light exit opening is formed.

4. The trackball module according to claim 1, wherein the light source is configured to maintain output of light, to blink, or to cease output of light according to a setting mode.

5. The trackball module according to claim 1, wherein the light source is configured to emit light with different colors in accordance with a setting mode or user manipulation of the trackball.

6. The trackball module according to claim 1, wherein the light source is configured to:
 emit light while an external device connected thereto operates,
 emit light as a pulse while waiting for a subsequent operation after completion of a previous operation, and
 stop emitting light while all operations are stopped, according to a setting mode.

7. A trackball module, comprising:
 a light source;
 a support comprising a light exit surface through which light emitted from the light source passes while being reflected at least once and is emitted to an outside of the trackball module; and
 a trackball disposed at the light exit surface of the support, supported by the support, and configured to receive a control command from a user,
 wherein light passing through the support is emitted to the outside of the trackball module via a side of the trackball, and
 wherein the support further comprises an optical passage having a step-like shape formed between two plates.

8. The trackball module according to claim 7, wherein the support includes a transparent or semi-transparent material.

9. The trackball module according to claim 7, wherein the trackball includes an opaque or semi-transparent material.

* * * * *